US006683057B1

(12) United States Patent
Koch et al.

(10) Patent No.: US 6,683,057 B1
(45) Date of Patent: *Jan. 27, 2004

(54) METHOD OF INHIBITING SMOOTH MUSCLE CELL PROLIFERATION

(75) Inventors: Walter J. Koch, Durham, NC (US); Robert J. Lefkowitz, Durham, NC (US); Per-Otto Hagen, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/400,861

(22) Filed: Sep. 21, 1999

Related U.S. Application Data

(63) Continuation of application No. 08/943,208, filed on Oct. 3, 1997, now Pat. No. 5,981,487.
(60) Provisional application No. 60/027,775, filed on Oct. 4, 1996.

(51) Int. Cl.[7] .................. A01N 43/04; A01N 37/18; A61K 31/70; A61K 38/00
(52) U.S. Cl. ................. 514/44; 514/12; 514/2
(58) Field of Search ................. 514/12, 2, 44

(56) References Cited

U.S. PATENT DOCUMENTS

| 5,624,936 A | 4/1997 | deSolms | |
|---|---|---|---|
| 5,981,487 A | * 11/1999 | Koch et al. | 514/12 |

FOREIGN PATENT DOCUMENTS

| EP | 0351921 | 1/1990 |
| EP | 0453119 | 10/1991 |

OTHER PUBLICATIONS

Inglese et al., Structure and mechanism of the G protein–coupled receptor kinases, 1993, The Journal of Biological Chemistry, vol. 268, pp. 23735–23738.*
Kass–Eisler et al. Quantitative determination of adenovirus–mediated gene delivery to rat cardiac myocytes in vitro and in vivo, vol 90, PNAS, 1993.*
Pitcher et al, "Role of βγ Subunits of G Proteins in Targeting the β–Adrenergic Receptor Kinase to Membrane–Bound Receptors", Science 257:1264–1267 (1992).
Koch et al, "The Binding Site for the βγ Subunits of Heterotrimeric G Proteins on the β–Adrenergic Receptor Kinase", The Journal of Biological Chemistry 286(11):8256–8260 (1993).
Boekhoff et al, "Olfactory Desensitization Requires Membrane Targeting of Receptor Kinase mediated by βγ–Subunits of Heterotrimeric G Proteins", The Journal of Biological Chemistry 269(1):37–40 (1994).
Koch et al, "Direct evidence that $G_i$–coupled stimulation of mitogen–activated protein kinase is mediated by $G_{\beta\gamma}$ activation of p21$^{ras}$", Proc. Natl. Acad. Sci. USA 91:12706–12710 (1994).
Luttrell et al, "$G_{\beta\gamma}$ Subunits Mediate Mitogen–activated Protein Kinase Activation by the Tyrosine Kinase Insulin–like Growth Factor 1 Receptor", The Journal of Biological Chemistry 270(28);16495–16498 (1995).
Hawes et al, "District Pathways of $G_i$–and $G_q$–mediated Mitogen–activated Protein Kinase Activation", The Journal of Biological Chemistry 270(29): 17148–17153 (1995).
Irani et al, "Ras proteins regulate multiple migotenic pathways in A/O vascular smooth muscle cells", Biochem. Biophys. Res. Comm. 202:1252 (1994).
Laugwitz et al, "Characterization and inhibition of β–adrenergic receptor kinase in intact myocytes", Cardiovascular Research 35:324–333 (1997).
Xu et al, "The N terminus of phosducin is involved in binding of βγ subunits of G protein", Proc. Natl. Acad. Sci. USA 92:2086–2090 (1995).
Koch et al, "Cellular Expression of the Carboxyl Terminus of a G Protein–coupled Receptor Kinase Attenuates Gβγ–medicated Signaling", The Journal of Biological Chemistry 269(8):6193 6197 (1994).
Inglese et al (1994) Functionally Active Targeting Domain of the Beta–adrenergic Receptor Kinase Icon Inhibition of G Beta–gamma Medicated Stimulation of Ttype II Adamanyl–cyclase. , Proc. Natl. Accad. Sci. 91:136–37.
Crystal, "Transfer of Genes to Humans, Early Lessons and Obstacles to Success", Science 270:404–410 (1995).
Marshall, "Less Hype, More Biology Needed for Gene Therapy", Science 270:1751 (1995).
Coghlan, "Gene dream fades away", New Scientist 148:14–15 (1995).
Günsburg et al, "Virus vector design in gene therapy", Molecular Medicine Today pp. 410–417 (1995).
Froecking et al, "Powerful and versatile enhance–promoter unit for mammalian expression vectors", Gene 45:101–105 (1986).
Lee et al, "Cardiac and Pulmonary Replacement", J. Thoracic Cardiovascular Surgery 111(1):246–252 (1996).
Fuller et al, "Genetic Engineering of Cardiac Muscle Cells: In Vitro and In Vivo", Genetic Engineering 16:17–27 (1994).
Luckow et al, "CAT constructions with multiple unique restriction sites for the functional analysis of eukaryotic promoters and regulatory elements", Nucleic Acids Research 15(13):5490 (1987).
Ngo et al, "Computational Complexity, Protein Structure Prediction, and the Levinthal Paradox", The Protein Folding Problem and Tertiary Structure Prediction, K. Merz, Jr. and S. Le Grand, Editors, Birkhauser Bost Inc., pp. 491–495 (1994).

(List continued on next page.)

Primary Examiner—Remy Yucel
Assistant Examiner—Konstantina Katcheves
(74) Attorney, Agent, or Firm—Nixon & Vanderhye P.C.

(57) ABSTRACT

The present invention relates, in general, to vascular smooth muscle proliferation and, in particular, to a method of inhibiting arterial and venous smooth muscle proliferation resulting, for example, from arterial injury or vein grafting. The invention also relates to an expression construct encoding a Gβγ inhibitor suitable for use in such a method.

26 Claims, 4 Drawing Sheets

OTHER PUBLICATIONS

Dillon, "Regulating gene expression in gene therapy", TIBTECH 11:167–173 (1993).

Rigby, "Gene therapy: a long and winding road", Current Opinion in Genetics and Development 5:397–398 (1995).

Orkin et al, "Report and Recommendations of the Panel to Assess the NIH Investment in Research on Gene Therapy", pp. 1–50, Dec. 7, 1995.

Akhter et al, "Restoration of β–adrenergic signaling in failing cardiac ventricular myocytes via adenoviral–mediated gene transfer", Proc. Natl. Acad. Sci. USA 94:1–6 (1997).

Lilly et al, "Intracoronary Administration Of Adenovirus For Gene Transfer Into Adult Rabbit Myocardium", Surgical Forum, pp. 279–281 (19s.

Drazner et al, "Potentiation of β–Adrenergic Signaling by Adenoviral–mediated Gene Transfer in Adult Rabbit Ventricular Myocytes", J. Clin. Invest. 99(2):288–296 (1997).

Hawes et al, "Determination of the Gβγ–binding Domain of Phosducin", The Journal of Biological Chemistry 269(47):29825–29830 (1994).

Kobilka et al., "cDNA for the human $β_2$–adrenergic receptor: A protein with multiple . . . " Proc. Nat. Acad. Sci. USA, vol. 84, Jan. 1987, pp. 46–50.

Kass–Eisler et al., "Quantitative determination of adenovirus–mediated gene delivery . . . " Proc. Natl. Acad. Sci. USA, vol. 90, Dec. 1993, pp. 11498–11502.

Stratford–Perricaudet et al., "Widespread Long–Term Gene Transfer to Mouse Skeletal . . . " J. Clin. Invest., vol. 90, Aug. 1992. pp. 626–630.

Guzman et al., "Efficient Gene Transfer into Myocardium by Direct Injection of Adenovirus Vectors." Circulation Research, vol. 73, 1993, pp. 1202–1207.

Bertin et al., "Specific atrial overexpression of G protein coupled human β. adrenoceptors . . . " Cardiovascular Research, vol. 27, 1993, pp. 1606–1612.

Metzger et al, "Skeletal troponin C reduces contractile sensitivity to acidosis in cardiac . . . " Proc. Natl. Acad. Sci. USA, vol. 90, Oct. 1993, pp. 9036–9040.

Ren et al., "Constitutively Active Mutants of the α–Adrenergic Receptor," The Journal of Biological Chemistry, vol. 268, No. 22, Aug. 5, 1993, pp. 16483–16487.

Pauletto et al., "Propranolol–induced changes in ventricular isomyosin composition in the rat." American Heart Journal, vol. 109, Jun. 1985, pp. 1269–1273.

Bristow et al., "Decreased Catecholamine Sensitivity and β–Adrenergic–Receptor . . . " The New England Journal of Medicine, vol. 307, No. 4, Jul. 22, 1982, pp. 205–211.

Bristow et al., β–Adrenergic Function in Heart Muscle Disease and Heart Failure. J. Mol. Cell. Cardiol. 17 (Supp. 2), 1985, pp. 41–52.

Bristow et al., "β–Adrenergic Pathways in Nonfailing and Failing Human Ventricular Myocardium," Circulation vol. 82 (Suppl. I), 1990, pp. I–12–I–25.

Fowler et al., "Assessment of the β–adrenergic receptor pathway in the intact falling human heart: . . ." Circulation, vol. 74, No. 6, Dec. 1986, pp. 1290–1302.

Ungerer et al., "Altered Expression of β–Adrenergic Receptor Kinase and ≈–Adrenergic . . . " Circulation, vol. 87, 1993, pp. 454–463.

Koch et al., "The Binding Site for the βτ Subunits of Heterotrimeric G Proteins . . . " The Journal of Biological Chemistry, vol. 268, No. 11, Apr. 15, 1993, pp. 8256–8260.

Benovic et al., "β–Adrenergic Receptor Kinase: Primary Structure Delineates a Multigene Family," Science, vol. 246, Oct. 13, 1989, pp. 235–240.

Hausdorff et al., "Turning off the signal: desensitization of β–adrenergic receptor function." The FASEB Journal, vol. 4, Aug. 1990, pp. 2881–2889.

Lohse et al., "Multiple Pathways of Rapid $β_2$–Adrenergic Receptor Desensitization." The Journal of Biological Chemistry, vol. 265, No. 6, Feb. 25, 1990, pp. 3202–3209.

Inglese et al., "Structure and Mechanism of the G Protein–coupled Receptor Kinases." The Journal of Biological Chemistry, vol. 268, No. 32, Nov. 15, 1993, pp. 23735–23758.

Ng et al., "Cardiac Myosin Heavy Chain mRNA Expression and Myocardial Function in the Mouse Heart," Circulation Research, vol. 68, No. 6, June 1991, pp. 1742–1750.

Medford et al., "Molecular Mechanisms Regulating VCAM–1, ICAM–1 and E–Selectin Gene Expression in Human Aortic Smooth Muscle Cells", Clinical Research, vol. 41, No. 2, 1993, p. 145A.

Pitcher et al., "Role of βτ Subunits of G Proteins in Targeting the β–Adrenergic . . . ", Science, vol. 247, Aug. 28, 1992, pp. 1264–1267.

Yatani et al., "A G Protein Directly Regulates Mammalian Cardiac Calcium Channels." Science vol. 238, Nov. 1987, pp. 1288–1292.

* cited by examiner

Bovine Minigene Protein seq -> 1-phase Translation

DNA sequence    591 b.p.    atgggaatcaag ... aacggcctctga    linear

```
                βARK 1
1/1             Gly 495                         31/11
atg gga atc aag cta ctg gac agt gac cag gag ctc tac cgc aac ttc ccc ctg acc atc
Met gly ile lys leu leu asp ser asp gln glu leu tyr arg asn phe pro leu thr ile
61/21                                           91/31
tcg gag cgg tgg cag cag gag gta gca gag act gtc ttt gac acc atc aat gct gag acg
ser glu arg trp gln gln glu val ala glu thr val phe asp thr ile asn ala glu thr
121/41                                          151/51
gac cgg ctg gag gcc cgc aag aaa acc aaa aac aag cag ttg ggc cac gag gaa gac tac
asp arg leu glu ala arg lys lys thr lys asn lys gln leu gly his glu glu asp tyr
181/61                                          211/71
gcc ctg ggc aag gac tgc atc atg cat ggc tac atg tcc aag atg ggc aac ccc ttc ctg
ala leu gly lys asp cys ile met his gly tyr met ser lys met gly asn pro phe leu
241/81                                          271/91
acc cag tgg cag cgg cgg tac ttc tac ctg ttc cct aac cgg ctc gag tgg cgg ggc gag
thr gln trp gln arg arg tyr phe tyr leu phe pro asn arg leu glu trp arg gly glu
301/101                                         331/111
ggc gag gcc ccg cag agc ctg ctg acc atg gag gag atc cag tcg gtg gag gag acg cag
gly glu ala pro gln ser leu leu thr met glu glu ile gln ser val glu glu thr gln
361/121                                         391/131
atc aag gag cga aag tgc ctc ctc ctc aag atc cga ggt ggc aag cag ttt gtc ctg cag
ile lys glu arg lys cys leu leu leu lys ile arg gly gly lys gln phe val leu gln
421/141                                         451/151
tgc gat agt gac cca gag ctg gtg cag tgg aag aag gag ctt cga gac gcc tac cgc gag
cys asp ser asp pro glu leu val gln trp lys lys glu leu arg asp ala tyr arg glu
481/161                                         511/171
gcc cag cag cta gtg cag cgg gtg ccc aag atg aag aac aag ccg cgc tcg ccc gtc gtg
ala gln gln leu val gln arg val pro lys met lys asn lys pro arg ser pro val val
541/181                                         571/191
gag ctg agc aag gtg cca ctg atc cag cgc ggc agt gcc aac ggc ctc tga
glu leu ser lys val pro leu ile gln arg gly ser ala asn gly leu stop
                                                              βARK 1
                                                              Leu 689
```

*Fig. 1*

METHOD OF INHIBITING SMOOTH MUSCLE CELL PROLIFERATION

This is a continuation of application Ser. No. 08/943,208, filed Oct. 3, 1997, now U.S. Pat. No. 5,981,487 now pending, the entire content of which is hereby incorporated by reference in this application.

This application claims priority from U.S. provisional Application Ser. No. 60/027,775, filed Oct. 4, 1996, the entire contents of which is incorporated herein by reference.

This invention was made with Government support under Grant No. HL-15448 awarded by the National Institutes of Health (NIH). The Government has certain rights in the invention.

TECHNICAL FIELD

The present invention relates, in general, to vascular smooth muscle proliferation and, in particular, to a method of inhibiting arterial and venous smooth muscle proliferation resulting, for example, from arterial injury or vein grafting. The invention also relates to an expression construct encoding a Gβγ inhibitor suitable for use in such a method.

BACKGROUND

Several growth factors that induce cellular mitogenesis and proliferation act through membrane-embedded G protein-coupled receptors (GPCRs). GPCRs couple to, and stimulate, heterotrimeric G proteins which, upon activation, dissociate to Gα and Gβγ subunits. Both these molecules can transduce intracellular signals via activation of specific effect or proteins. The intracellular signaling events leading to cellular proliferation following GPCR-activation appear to be transduced largely through the activation of $p21^{ras}$ (Ras) and subsequent activation of the p42 and p44 mitogen-activated protein (MAP) kinases. Growth factors which act through GPCRs, such as lysophosphatidic acid (LPA) via the LPA receptor and norepinephrine via α2-adrenergic receptors, have been shown to activate Ras and MAP kinase primarily through Gβγ (Koch et al, Proc. Natl. Acad. Sci. USA 91:12706 (1994)).

The last 194 amino acids ($Gly^{495}$-$Leu^{689}$) of the bovine β-adrenergic receptor kinase-1 (βARK-1) represent a specific and selective Gβγ-inhibitor (see FIG. 1 for amino acid sequence of βARK-1-(495–689) and a nucleic acid sequence encoding same). βARK-1 is a Gβγ-dependent, cytosolic enzyme which must translocate to the membrane where it can phosphorylate its receptor substrate by physically binding to the membrane-anchored Gβγ (Pitcher et al, Science 257:1264 (1992)).

The peptide encoded by the plasmid designated βARK-1-(495–689) Minigene (which peptide is designated $βARK_{CT}$) contains the specific Gβγ-binding domain of βARK-1 (Koch et al, J. Biol. Chem. 268:8256 (1993)). When cells are transfected with the βARK-1-(495–689) Minigene (that is, the $βARK_{CT}$ Minigene), or peptides containing the Gβγ-binding domain of βARK-1 are introduced into cells, several Gβγ-dependent processes are markedly attenuated including βARK-1-mediated olfactory receptor desensitization (Boekhoff et al, J. Biol. Chem. 269:37 (1994)), phospholipase C-β activation (Koch et al, J. Biol. Chem. 269:6193 (1994)) and Gβγ-dependent activation of Type II adenylyl cyclase (Koch et al, Biol. Chem. 269:37 (1994)). These studies demonstrate that the βARK-1-(495–689) peptide (that is, $βARK_{CT}$) is Gβγ-specific, that is, that it does not alter Gα-mediated responses (Koch et al, Proc. Natl. Acad. Sci. USA 91:12706 (1994); Koch et al, Biol. Chem. 269:37 (1994)). A further study utilizing the $βARK_{CT}$ Minigene has demonstrated that the growth factor IGF-1, by binding to its specific receptor, activates the Ras-MAP kinase pathway via Gβγ. These results indicate that certain receptor-tyrosine kinase-mediated cascades include a Gβγ component, as do those for LPA and other agonists that activate classical GPCRs (Luttrell et al, J. Biol. Chem. 270:16495 (1995)).

The present invention is based, at least in oart, on the observation that the $βARK_{CT}$ peptide mediates inhibition of Gβγ function in vivo and that, in smooth muscle cells, that inhibition is associated with a modulation of cell proliferation.

OBJECTS AND SUMMARY OF THE INVENTION

It is a general object of the invention to provide a method of inhibiting smooth muscle proliferation.

It is a specific object of the invention to provide a method of inhibiting uncontrolled smooth muscle cell proliferation by inhibiting Gβγ-signaling.

It is another object of the invention to provide a method of reducing intimal hyperplasia following vein grafting and restenosis following arterial injury.

The foregoing objects are met by the method of the present invention which comprises introducing into smooth muscle cells at a body site an agent that inhibits Gβγ-mediated processes and thereby inhibits proliferation of the muscle cells. In one embodiment, the agent comprises a nucleic acid encoding a polypeptide corresponding to the Gβγ-binding domain of βARK. In accordance with this embodiment, the nucleic acid is introduced into the cells in a manner such that the polypeptide is produced and proliferation of the smooth muscle cells is inhibited.

Further objects and advantages of the invention will be clear from the description that follows.

BRIEF DESCRIPTION OF THE DRAWINGS

FIG. 1. Amino acid sequence of $βARK_{CT}$ (that is, βARK-1-(495–689)) polypeptide and nucleic acid sequence encoding same (SEQ ID NO:2 and SEQ ID NO:1, respectively).

DETAILED DESCRIPTION OF THE INVENTION

Figure 2:
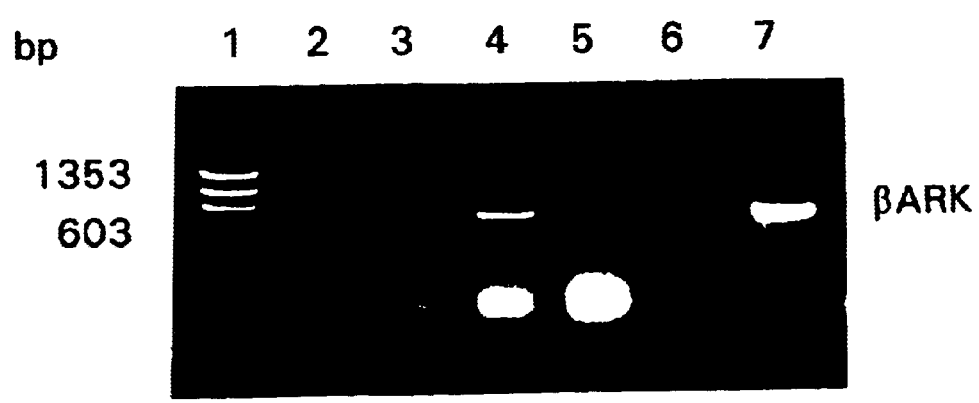
FIG. 2. RT PCR results from 3 day vein grafts treated with empty pRK5 and pRK $βARK_{CT}$. Lane 1 Φ×174HaeIII digested DNA markers with 2 of the size marker positions listed at the left; lanes 2 and 3, two control vein grafts transfected with pRK5 (plasmid); lanes 4 and 5, two vein grafts transfected with pRK $βARK_{CT}$; lane 6 negative control for PCR; lane 7, amplification of the positive control pRK $βARK_{CT}$purified plasmid. This gel displays two of each of the four 3 day vein grafts tested by RT PCR for transgene expression.

Smooth muscle proliferation is problematic in several clinical settings including intimal hyperplasia following vein grafting (Davies and Hagen, Br. J. Surg. 81:1254 (1994)) and restenosis following arterial angioplasty (Epstein et al, J. Am. Coll. Cardiol. 23:1278 (1994); French et al, Circulation 90:2402 (1994)). Smooth muscle cell proliferation is also associated with the development of atherosclerotic lesions (Katsuda et al, Amer. J. Pathol. 142:1787 (1993)). Smooth muscle cell proliferation can also be a problem when it occurs in the airways (Schramm et al, Life Sci. 59:PL9 (1996)), for example, in asthmatic patients and in individuals with idiopathic pulmonary fibrosis (Kanematsu et al, Chest 105:339 (1994)). The present invention provides a method of controlling smooth muscle proliferation in such settings by inhibiting Gβγ-dependent processes.

More specifically, the present invention provides a method of inhibiting smooth muscle proliferation at a body site comprising introducing into smooth muscle cells at the site an agent that effects inhibition of Gβγ-mediated processes. In one embodiment, the agent is a nucleic acid sequence that encodes a polypeptide that specifically inhibits Gβγ-dependent processes. One such agent is a nucleic acid encoding the Gβγ-binding domain of βARK.

As one example, the present invention relates to a nucleic acid that encodes the last 194 amino acids of βARK-1, e.g., the amino acid sequence given in FIG. 1. Inhibitory portions of this polypeptide can also be used, for example, the 125 amino acid portion from position 546–670 of the FIG. 1 sequence (corresponding to amino acids 53–177 of SEQ ID NO:2) or the 28 amino acid portion from position 643–670 of the FIG. 1 sequence (corresponding to amino acids 150–177 of SEQ ID NO:2). Methods that can be used to identify βARK(1 and 2) fragments that inhibit Gβγ-dependent processes are described by Koch et al, J. Biol. Chem. 268:8256 (1993) (see also Touhara et al, J. Biol. Chem. 270:17000 (1995); Inglese et al, Proc. Natl. Acad. Sci USA 91:3637 (1994); Luttrell et al, J. Biol. Chem. 270: 16495 (1995); Hawes et al, J. Biol. Chem. 270:17148 (1995); Koch et al, Proc. Natl. Acad. Sci. USA 91:12706 (1994)). In one aspect of this example, the nucleic acid has the sequence also given in FIG. 1 (SEQ ID NO:1). Additionally, nucleic acids suitable for use in the present invention include those encoding functional equivalents of the polypeptide shown in FIG. 1 (SEQ ID NO:2), and portions thereof, that is, polypeptides that specifically inhibit binding of βARK to Gβγ.

In addition to the βARK fragments described above, fragments of the 33 Kda Gβγ-binding retinal phosphoprotein, phosducin, can also be used. Examples of fragments of phosducin suitable for use in the present invention, and methods of selecting same, are described by Xu et al, Proc. Natl. Acad. Sci. USA 92:2086 (1995) and Hawes et al, J. Biol. Chem. 269:29825 (1994). Suitable nucleic acid sequences encoding these peptides will be apparent to one skilled in the art.

In accordance with the present invention, the nucleic acid described above can be present in a recombinant molecule which can be constructed using standard methodologies. The recombinant molecule comprises a vector and the nucleic acid encoding the inhibitor. Vectors suitable for use in the present invention include plasmid and viral vectors. Plasmid vectors into which the nucleic acid can be cloned include any plasmid compatible with introduction into smooth muscle cells. Such vectors include mammalian vectors such as pRK5. Viral vectors into which the nucleic acid can be introduced include adenoviral vectors (see Examples II and III), retroviral vectors, and adenoassociated viral vectors. The nucleic acid of the invention can be present in the vector operably linked to regulatory elements, for example, a promoter. Suitable promoters include, but are not limited to, the CMV, TK and SV40 promoters. Smooth muscle cell specific promoters can also be used, for example, an αSM22 promoter (see Moessler et al, Develop. 122:2415 (1996)).

In another embodiment of the present invention, a Gβγ inhibitor can be introduced directly into smooth muscle cells at a target site using methodologies known in the art. One such inhibitor is the polypeptide corresponding to the Gβγ-binding domain of βARK, for example, amino acids $Gly^{495}$-$Leu^{689}$ of βARK-1. Other suitable peptides of both βARK and phosducin are described above as are references disclosing methods suitable for use in selecting inhibitory peptides. The Gβγ inhibitor can be introduced into the target cells in a form substantially free of any proteins with which it may normally be associated. Polypeptide inhibitors can be produced recombinantly using the nucleic acid described above or chemically using known methods.

Compositions

The present invention also relates to pharmaceutically acceptable compositions comprising the nucleic acid or polypeptide of the invention. Such compositions can include, as active agent, the inhibitor or inhibitor-encoding sequence, in combination with a pharmaceutically acceptable carrier (e.g., water, phosphate buffered saline, etc.). The amount of active agent present in the composition can vary with the inhibitor or encoding sequence, the delivery system (in the case of a nucleic acid), the patient and the effect sought. Likewise, the dosing regimen can vary depending, for example, on the delivery system (particularly when a nucleic acid is used), the composition and the patient.

Therapy

The present invention relates to the use in gene therapy regimens of a nucleic acid (e.g., a DNA sequence) encoding a Gβγ inhibitor, for example, a polypeptide corresponding to the βARK Gβγ-binding domain, or portions thereof as defined above.

Delivery of the nucleic acid of the invention can be effected using any of a variety of methodologies, including transfection with a plasmid or viral vector, such as those described above (see, for example, Steg et al, Circulation 90:1640 (1994), Guzman et al, Circulation 88:2838 (1993), Lee et al, Circulation Res. 73:797 (1993) and Plautz et al, Circulation 83:578 (1991)), or fusion with a lipid (e.g., a liposome) (see Takeshita et al, J. Clin. Invest. 93:652 (1994), Chapman et al, Cir. Res. 71:27 (1992), LeClerc et al, J. Clin. Invest. 90:936 (1992) and Nabel et al, Human Genet. 3:649 (1992)). Upon introduction into target cells, the nucleic acid is expressed and the Gβγ inhibitor is thereby produced.

Target cells include smooth muscle cells present, for example, in veins, arteries or airways.

Introduction of the nucleic acid into the target cells can be carried out using a variety of techniques. In the case of vein grafting, the techniques set forth in Examples I and II that follow can be used. As described in Example I, prior to grafting, the vein graft can be contacted with a solution containing the nucleic acid encoding the Gβγ inhibitor. While in Example I the nucleic acid is present in an plasmid, other systems can be used to effect delivery, including those described above and in Example II. Alternatively, naked nucleic acid (e.g., naked DNA) present in a pharmaceutically acceptable carrier can be used.

In accordance with the present method, the graft is held in contact with the nucleic acid for a period of time (e.g., 20–30 minutes) sufficient to permit introduction of the nucleic acid into smooth muscle cells of the graft and under conditions that facilitate the introduction of the nucleic acid without unacceptably compromising viability of the graft. Optimum conditions can readily be determined by one skilled in the art (see Examples I and II below).

In the case of arterial smooth muscle cells, the nucleic acid, advantageously in a viral vector, can be administered to an actual injury site (including an atherosclerotic site) via a catheter, for example, a balloon catheter. In accordance with this approach, inhibition of restenosis following angioplasty can be effected as can inhibition of smooth muscle cell proliferation at other arterial injury (or atherosclerotic) sites. (See Example III.)

As indicated above, other target sites include airway smooth muscle cells. Nucleic acids of the invention can be delivered to such cells, for example, in a viral vector, via aerosol administration. Optimum conditions can be readily determined by one skilled in the art.

The therapeutic methodologies described herein are applicable to both humans and non-human mammals.

It will be appreciated from a reading of this disclosure that the present invention makes possible a variety of studies targeting G protein pathways. Further therapeutic modalities can be expected to result from such studies.

Screening

The demonstration that $\beta ARK_{CT}$ inhibits smooth muscle cell proliferation makes possible assays that can be used to identify other smooth muscle cell proliferation inhibitors. For example, compounds to be tested for their ability to inhibit smooth muscle cell proliferation can be contacted with a solution containing G$\beta\gamma$ (eg purified G$\beta\gamma$)and $\beta$ARK, or a G$\beta\gamma$ binding portion thereof (eg purified $\beta$ARK, or portion thereof), under conditions such that binding of G$\beta\gamma$ and $\beta$ARK, or binding portion thereof, can occur. Test compounds that inhibit that binding can be expected to inhibit smooth muscle cell proliferation. Such tests compounds can also be screened for their ability to inhibit smooth muscle cell proliferation by determining the effect of the presence of the compound on G$\beta\gamma$ activation of $\beta$ARK (eg using standard methodologies). A test compound that inhibits kinase activation can be expected to be suitable for use as an inhibitor of smooth muscle cell proliferation. Test compounds can also be screened by contacting cells (eg smooth muscle cells or fibroblasts) with such a compound and determining the effect of the test compound on LPA dependent activation of MAP kinase. A test compound that inhibits such activation can be expected to inhibit smooth muscle cell proliferation.

Certain aspects of the present invention are described in greater detail in the non-limiting Example that follows.

EXAMPLE I

Effect of $\beta ARK_{CT}$ on the Formation of Vein Graft Intimal Hyperplasia and Phenotypical Functional Alterations Experimental design: Forty New Zealand White rabbits underwent carotid interposition vein bypass grafting. Prior to grafting, veins were incubated in heparinized Ringer's lactate (controls; n=18), or plasmid solutions containing either $\beta ARK_{CT}$ (n=14; 190 $\mu$g/ml) or empty plasmid DNA (plasmid: n=8; 190 $\mu$g/ml) for 30 mins at 37° C. Twenty-four vein grafts (n=10 controls, n=6 plasmid, n=8 $\beta ARK_{CT}$) were harvested at 28 days by perfusion fixation. Intimal and medial dimensions of vein grafts were calculated by video-morphometry. Sections were taken for scanning and transmission electron microscopy (TEM). Ten vein grafts (n=5; control and $\beta ARK_{CT}$) were analyzed for in vitro contractile responses to norepinephrine and serotonin in the presence and absence of pertussis toxin (PTx) to categorize receptor G-protein receptor coupling. Six vein grafts (n=3; control and $\beta ARK_{CT}$) were harvested at 3 days for $\beta ARK$-1 protein and mRNA (RT-PCR) expression.

Transgene constructs: Gene transfer to the experimental vein grafts was done utilizing the previously described plasmid which contains cDNA encoding the last 194 amino acid residues (Met-Gly$^{495}$-Leu$^{689}$) (SEQ ID NO:2) of bovine $\beta ARK_{CT}$ (PRK-$\beta ARK_{CT}$) (Koch et al, Proc. Natl. Acad. Sci. USA 91:12706 (1994); Koch et al, J. Biol. Chem. 268: 8256 (1993)). This peptide contains the experimentally determined (Gln$^{546}$-Ser$^{670}$) (corresponding to amino acids 53–177 of SEQ ID NO:2) G$\beta\gamma$ binding domain. The empty pRK5 plasmid was used as the negative control as previously described (Koch et al, Proc. Natl. Acad. Sci. USA 91:12706 (1994); Koch et al, J. Biol. Bhem. 269:6193 (1994)). Large scale plasmid preparations of pRK5 and pRK $\beta ARK_{CT}$ were purified using Qiagen columns (Qiagen Inc., Chatsworth, Calif.) prior to vein graft gene transfer.

Analysis Of $\beta ARK_{CT}$ transgene expression: Three day vein grafts were utilized for analysis of specific transgene expression. $\beta ARK_{CT}$ mRNA expression was determined by standard methods of reverse transcriptase-polymerase chain reaction (RT-PCR) (Ungerer et al, Circularion 87:454 (1993)) using a RT-PCR kit utilizing TaqPlus DNA Polymerase (Stratagene Inc. La Jolla, Calif.). Total RNA was first isolated using the single step reagent RNAzol (Biotecx Inc., Houston, Tex.) (Chomezynski et al, Anal. Biochem. 161: 156 (1987))) and treated with DNase I to eliminate any possible plasmid contamination. A $\beta ARK_{CT}$ primer set was utilized to specifically amplify $\beta ARK_{CT}$ mRNA. The primers utilized were as follows: sense primer (corresponding to the start of $\beta ARK_{CT}$) 5'-GAATTCGCCGCCACCATGGG-3' (SEQ ID NO:3); antisense primer (corresponding to the $\beta$-globin untranslated region linked to the end of the $\beta ARK_{CT}$ cDNA (Koch et al, J. Biol. Chem. 269:6193 (1994)) 5'-GGAACAAAGGAACCTTTAATAG-3' (SEQ ID NO:4). This primer set amplifies a 670 base pair fragment corresponding to $\beta ARK_{CT}$ mRNA.

Operative Procedure: Anesthesia was induced and maintained with subcutaneously injected ketamine hydrochloride (60 mg/kg, Ketaset, Bristol Laboratories, Syracuse, N.Y.) and xylazine (6 mg/kg, Anased, Lloyd Laboratories, Shenandoah, Iowa). Antibiotic prophylaxis with 30,000 IU/kg of benzanthine and procaine penicillin (Durapen, Vedco Inc., Overland Park, Kans.) was given intramuscularly at the time of induction. Surgery was performed using an operating microscope (JKH 1402, Edward Weck Inc., Research Triangle Park, N.C.) under sterile conditions. After exposure through a midline longitudinal neck incision, the right external jugular vein was identified, its branches were diathermied at a distance from the vein to minimize injury and it was then dissected out. Following excision, the vein was kept moist in a heparinized Ringer lactate solution (5 IU/ml, Heparin, Elkins-Sinn Inc., Cherry Hill, N.J.) for approximately 15 minutes while the right common carotid artery was identified, dissected and both proximal and dismal control obtained. Heparin (200 IU/kg) was administered intravenously. A proximal longitudinal arteriotomy was made and one end of the reversed jugular vein was anastomosed to the artery in an end-to-side manner using continuous 10-O microvascular monofilament nylon suture (Ethilon, Ethicon Inc., Somerville, N.J.). The distal anastomosis was performed in a similar manner. Throughout the procedure, care was taken to avoid unnecessary instrumentation of the vein graft. The right common carotid was ligated and divided between the two anastomoses with 4-O silk sutures and the wound closed in layers.

Morphology: Three vein grafts were harvested 28 days after surgery. Following isolation and systemic heparinization (200 IU/kg, i.v.), the vein grafts were perfusion fixed in situ at 80 mmHg with an initial infusion of Hanks Balanced Salt Solution (HBSS, Gibco Laboratories, Life Technologies Inc., Grand Island, N.Y.) followed by 2% glutaraldehyde made up in 0.1 M cacodylate buffer (pH 7.2) supplemented with 0.1 M sucrose to give an osmolality of approximately 300 mOsm. After 60 minutes, the specimen was removed, immersed in the glutaraldehyde fixative for a further 24 hours. Cross-sections from the mid-portion of the vein graft were processed for light microscopy. Following standard histological procedures, each specimen was stained with a modified Masson's trichrome and Verhoeff's elastin stain and dimensional analysis was performed by videomorphometry (Innovision 150, American Innovision Inc., San Diego, Calif.). The intima and media were delineated by identification of the demarcation between the criss-cross orientation of the intimal hyperplastic smooth muscle cells and circular smooth muscle cells of the media and the outer limit of the media was defined by the interface between the circular smooth muscle cells of the media and the connective tissue of the adventida. The thickness of each layer was also determined. A ratio of the intimal and medial areas (intimal ratio=intimal area/[intimal+medial areas]) and a luminal diameter to cross-sectional wall thickness (luminal index= luminal diameter/[cross-sectional wall thickness]) was calculated.

In vitro contractile studies: Under anesthesia, the original incision was re-opened and the jugular vein and vein graft isolated. The midpart of each vessel was sectioned in situ into two 5 mm segments and excised. These rings were suspended immediately from two stainless steel hooks in 5 ml organ baths containing oxygenated Krebs solution (122 mM NaCl, 4.7 mM KCl, 1.2 mM $MgCl_2$, 2.5 mM $CaCl_2$, 15.4 mM $NaHCO_3$, 1.2 mM $KH_2PO_4$ and 5.5 mM glucose; maintained at 37° C. and bubbled with a mixture of 95%) $O_2$ and 5% $CO_2$). One hook was fixed to the bottom of the bath and the other was connected to a force transducer (Myograph F-60, Narco Bio-Systems, Houston, Tex.). The isometric responses of the tissue were recorded on a multichannel polygraph (Physiograph Mk111-S, Narco Bio-Systems, Houston, Tex.). The tissues were then placed under 0.5 grams tension and allowed to equilibrate in physiologic Krebs solution for one hour. During the equilibration period, the Krebs solution was replaced every 15 minutes. Following equilibration, the resting tension was adjusted in 0.25 gram increments from 0.25 to 2.5 gram and the maximal response to a modified oxygenated Krebs solution (60 mM KCl, 66.7 mM NaCl, 1.2 mM $MgCl_2$, 2.5 mM $CaCl_2$, 15.4 mM $NaHCO_3$, 1.2 mM $KH_2PO_4$ and 5.5 mM glucose) was measured at each resting tension to establish a length-tension relationship. Based on these results, the optimal resting tension for each ring (the tension at which the response to the modified Krebs solution was maximal) was determined and the ring was set at this tension for subsequent studies. Norepinephrine ($10^{-9}$ to $10^{-4}$M) was added cumulatively in half molar increments and the isometric tension developed by the tissue was measured. After washout and re-equilibration, dose response curves were obtained for serotonin ($10^{-9}$ to $10^{-4}$M). The responses to each agonist were assessed with and without the presence of PTx (100 ng/ml pre-incubated for 60 minutes) (Davies et al, J. Clin. Invest. 94:1680 (1994)). All compounds were obtained from Sigma Chemical Company (St. Louis, Mo.).

Data and Statistical Analysis: The $EC_{50}$ value, the concentration for the half maximal response, for each agonist in each ring was calculated by logistic analysis and is expressed as loglo [$EC_{50}$] (Finney, Statistical methods in biological assay. London: Charles Griffin, pp. 349–369 (1978)). All data are presented as the mean±standard error of the mean (s.e.m.) and statistical differences between groups were tested by ANOVA with post hoc Tukey-Kramer multiple comparison tests for the functional studies and with a Kruskal-Wallis nonparametric ANOVA with post hoc Dunn's multiple comparison tests for the morphometric data.

Results

Transgene expression: Successful transfection of the vein grafts was demonstrable at three days after surgery. $\beta ARK_{CT}$ mRNA was specifically amplified from DNase I treated total RNA using RT-PCR from vein grafts treated with pRK-$\beta ARK_{CT}$ while control grafts treated with the empty pRK5 plasmid showed no transgene expression (FIG. 2). Since the amount of tissue available is small, protein immunoblotting for $\beta ARK_{CT}$ peptide expression was not possible.

Intimal hyperplasia: All animals survived to 28 days, and all grafts were patent at harvest. Microscopically, the luminal surfaces of the vein grafts from each group were covered by a layer of intact endothelial cells, beneath which lay a hyperplastic intima with the smooth muscle cells of the intimal hyperplasia arranged in a crisscross pattern with little extracellular matrix. The medial smooth muscle cells in the grafts from each group appeared slender, were arranged in a circular pattern, and contained a greater amount of extracellular matrix suggestive of medial hypertrophy. At 28 days, there was a significant 37% reduction in intimal thickness in $\beta ARK_{CT}$ vein grafts (45±4 μm) compared to either plasmid (69±3 μm) or control (70±4 μm) vein grafts without a significant change in medial thickness (70±4 μm, 65±5 μm and 77±3 μm, respectively). Dimensional analysis of the control and treated groups is shown in Table I. There was a 52% decrease in intimal area (Table I) while the medial area was unchanged in the $\beta ARK_{CT}$ compared to the plasmid treated vein grafts (Table I). The intimal ratio was significantly reduced in the $\beta ARK_{CT}$ vein grafts (p<0.01; 0.36±0.02, mean±s.e.m.) compared to either plasmid (0.54±0.02) or control vein grafts (0.52±0.02). The luminal area of the $\beta ARK_{CT}$ treated vein grafts was 41% less than the plasmid treated vein grafts while the luminal indices were not significantly different for the control, plasmid and $\beta ARK_{CT}$ vein grafts.

TABLE I

Dimensional Analysis

| | Control | Plasmid | $\beta ARK_{CT}$ | p-value |
|---|---|---|---|---|
| Lumen (mm²) | 20.5 ± 1.5 | 28.6 ± 4.01 | 16.6 ± 2.33† | 0.02 |
| Intima (mm²) | 1.14 ± 0.09 | 1.29 ± 0.12 | 0.62 ± 0.03† | 0.01 |
| Media (mm²) | 1.08 ± 0.11 | 1.29 ± 0.17 | 1.12 ± 0.10 | 0.18 |
| Intimal ratio | 0.52 ± 0.02 | 0.54 ± 0.02 | 0.36 ± 0.02* | 0.02 |
| Luminal Index | 39.4 ± 2.6 | 44.2 ± 3.1 | 37.8 ± 3.9 | 0.4 |

The area of the lumen, the intimal and the medial layers from control, plasmid and $\beta ARK_{CT}$ treated grafts. The intima ratio (intimal area/[intimal + medial areas]) and luminal index (luminal diameter/[cross-sectional wall thickness]) are also shown. Values are the mean ± s.e.m. Statistical Analysis is by Kruskal-Wallis nonparametric ANOVA with post hoc Dunn's multiple comparison tests (p < 0.05 vs. Control; †p < 0.05 vs. Plasmid)

Contractile function of experimental vein grafts: Control and $\beta ARK_{CT}$ treated vein grafts responded with concentration dependent contractions to the agonists norepinephrine and serotonin. In the presence of PTx at concentrations sufficient to produce 100% ADP ribosylation of G-proteins (Davies et al, J. Clin. Invest. 94:1680 (1994)), the contractile responses in control vein grafts to norepinephrine (p<0.01) and serotonin (p<0.01) were significantly reduced compared to untreated control vein grafts (Table II). This is the typical functional alteration seen in experimental vein grafts as native veins do not have a PTx sensitive component in their contractile responses to these G-protein coupled agonists. In contrast, the responses of the $\beta ARK_{CT}$ treated vein grafts to norepinephrine and serotonin were unchanged in the presence of PTx indicating the loss of a $G\alpha_i$ component (Table II).

TABLE II

Sensitivity of Contractile Responses

|  | Norepinephrine | Norepinephrine with pertussis toxin | Serotonin | Serotonin with pertussis toxin |
|---|---|---|---|---|
| Control | 6.00 ± 0.09 | 5.16 ± 0.09* | 6.34 ± 0.10 | 5.54 ± 0.26* |
| $\beta ARK_{CT}$ | 5.91 ± 0.19 | 5.81 ± 0.18 | 6.57 ± 0.10 | 6.55 ± 0.13 |

Data are expressed s the mean ± s.e.m.. Contractile sensitivity is shown as -logEC$_{50}$.
*p < 0.01 compared to corresponding pertussis toxin untreated vessel by ANOVA.

Electron microscopy of vein grafts: Scanning electron microscopy from both control vein grafts and vein graft transfected with empty plasmid showed the luminal surface to be lined with sharply outlined endothelial cells with well defined cell borders. Occasional junctional stomata were noted. Transmission electron micrograph of these vein grafts confirmed the presence of well formed endothelial cells, beneath which were well developed smooth muscle cells of both contractile (cytoplasm predominantly filled with contractile filaments) and synthetic phenotypes (cytoplasm filled with synthetic organelles) in a loose connective tissue matrix. No inflammatory cells or evidence for apoptosis was identified in these grafts. Scanning electron microscopy from vein grafts transfected with $\beta ARK_{CT}$ showed a similar picture to the control and plasmid transfected vein grafts with well preserved, normal appearing endothelial cells with occasional stomata at their junctions on the luminal surface. Transmission electron microscopy showed a similar ultrastructural pattern to the control and plasmid transfected vein grafts. One difference in the $\beta ARK_{CT}$ treated vein grafts was seen at higher magnification, which was the appearance of numerous cells with ultrastructural evidence of apoptosis with nuclear fragmentation, membrane disruption, and in places, disintegration products consisting of endoplasmic reticulum.

EXAMPLE II

Adenoviral Mediated Inhibition of Gβγ Signaling Limits Development of Intimal Hyperplasia Thirty-seven male NZW rabbits had interposition bypass grafting of the carotid artery using the jugular vein. Prior to grafting, veins were incubated in heparinized Ringer's lactate (controls; n=10), solutions containing adenoviral vectors ($1\times10^{10}$ PFU/ml) encoding $\beta ARK_{CT}$ (n=19), β-galactosidase (β-Gal; n=3), or empty vector (EV; n=3). (For details of adenoviral vector, see Drazner et al., J. Clin. Invest. 99:288 (1997).) After implantation, vein grafts were coated with 4 ml of 30% pluronic gel with or without the respective viral solutions ($1.7\times10^9$ PFU/ml).

The efficacy of $\beta ARK_{CT}$ transfection in vein grafts was verified by RT-PCR on days 3, 5 and 7 postoperatively (n=3 per time-point). To determine the cellular expression of the transfected gene, X-Gal staining for the marker gene β-Gal was performed on day 3. Positive (blue) cells were seen throughout the wall of the β-Gal vein grafts. At 28 days, the intimal thickness) in $\beta ARK_{CT}$ vein grafts (n=6) was reduced by 33% with no significant change in the medial thickness (MT), compared to control (n=6) and EV (n=3) grafts (Table III). Contractile studies showed enhanced sensitivity in response to norepinephrine (NE) and serotonin (5-HT) in 28 day $\beta ARK_{CT}$ vein grafts (n=4), as compared to controls (n=4) and EV (n=2), and insensitivity to pertussis toxin (PT) (Table III). Viral infection of vein grafts with EV did not alter vein grafts dimensions or contractility.

TABLE III

|  | IT (μm) | MT (μm) | NE | NE + PT | 5-HT | 5-HT + PT |
|---|---|---|---|---|---|---|
| $\beta ARK_{CT}$ | 57 ± 4* | 68 ± 3 | 6.35 ± 0.06† | 5.92 ± 0.25 | 6.74 ± 0.10† | 6.46 ± 0.19 |
| EV | 86 ± 10 | 87 ± 4 | 5.67 ± 0.03 | — | 5.65 ± 0.08 | — |
| Control | 85 ± 4 | 91 ± 5 | 5.85 ± 0.10 | 5.17 ± 0.14‡ | 6.17 ± 0.10 | 5.32 ± 0.18‡ |

Data are shown as mean ± S.E.M.
Sensitivity is defined as -logED$_{50}$.
*p < .05 compared to EV and control (Kruskal-Wallis with post-hoc Dunn's test);
†p < .01 compared to EV and control (ANOVA);
‡p < .001 compared to without PT (Student t-test).

The results demonstrate that inhibition of Gβγ signaling with adenoviral mediated $\beta ARK_{CT}$ in vivo transfection effectively modifies the structural and functional hyperplastic abnormalities in experimental vein grafts.

EXAMPLE III

Inhibition of Restenosis of Injured Carotid Artery with $\beta ARK_{CT}$ Adenovirus The rat common carotid injury is a well studied and reliable model of neo-initimal cell proliferation (Clowes et al, Lab. Invest. 49:327 (1983)). Following the application of a high pressure vascular damage, vascular smooth muscle cells migrate from the tunica media through the basal lamina into the tunica intima, were they proliferate. Those mechanisms are sustained by growth factor released from cells infiltrating the neo-intima and other substances circulating in the blood stream. At the vascular smooth muscle cells level, those factors interact with specific receptors thus activating intracellular mechanisms of proliferation. Among them, mitogen activated protein (MAP) kinase plays a relevant role, being at the confluence of several receptor activated pathways. It has been demonstrated recently that the βγ subunit of the heterotrimeric G protein mediates the activation of the MAP kinase induced by Gi coupled receptors. The carboxyterminus portion of the G coupled receptor kinase βARK1 binds the βγ subunit, thus inhibiting its signaling on MAP kinase.

Figure 3:
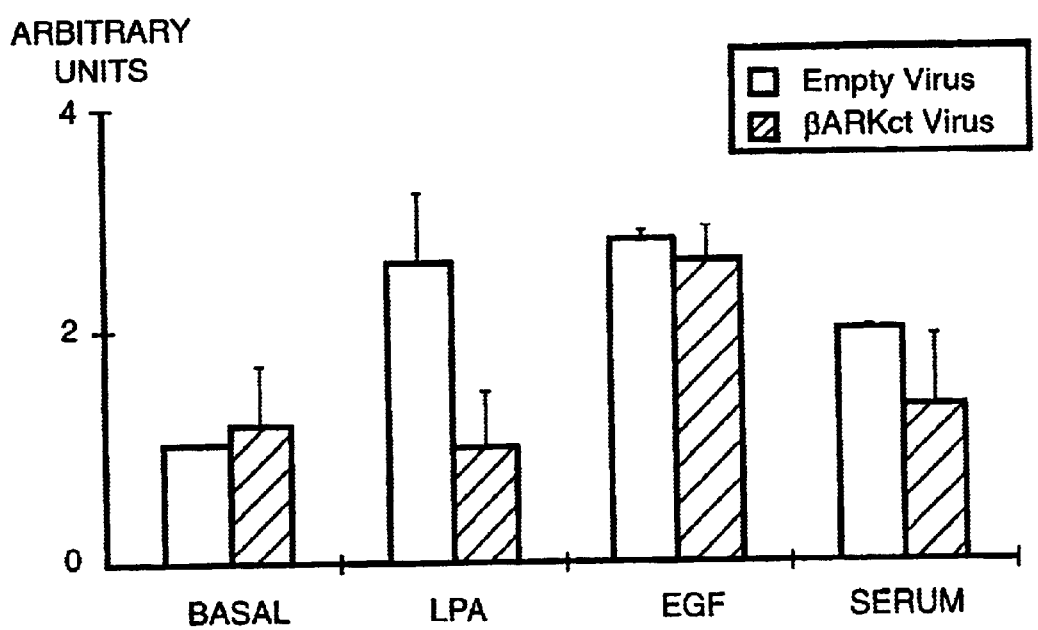
FIG. 3. MAP kinase activity in cultured vascular smooth muscle cells.

Using adenoviral mediated gene delivery (see Drazner et al., J. Clin. Invest. 99:288 (1997), it was possible to demonstrate that induction of expression of $\beta ARK_{CT}$ resulted in the inhibition of proliferation of vascular smooth muscle cells in the rat carotid injury model. Firstly, it was shown that in rabbit aortic smooth cells in culture (see Davies et al, J. Surg. Res. 63:128 (1996)), the virus was able to infect and replicate, resulting in the inhibition of the activation of MAP kinase in response to Gi coupled receptor stimulation. The lysophosphatidic receptor, a major mitogen circulating in the serum, was assessed. Furthermore, MAP kinase activation in response to fetal bovine serum and epidermal growth factor was assessed. $\beta ARK_{CT}$ adenovirus in the cultured vascular smooth muscle cells inhibited LPA (−58% of the same response observed in empty virus treated cells) and serum (−38%) activation of MAP kinase, without interfering with basal (+18%) and EGF (−7%) response (see FIG. 3).

The feasibility of infection of vascular smooth muscle cells in vivo was also determined using the rat common carotid after balloon injury. The balloon injury was performed through the external carotid in the common carotid by means of a Fogarty catheter with the balloon inflated at 1.5 atmospheres. After the injury, the virus ($0.5 \times 10^{10}$ PFU) was injected into the lumen of the common carotid through the external carotid and incubated for 30 min. The external carotid was then tied up by means of silk sutures and the blood flow in the common carotid was restored. A further dose of virus (~$0.5 \times 10^{10}$ PFU) was applied at the external of the common carotid by means of pluronic gel. The wound was closed in layers. A virus containing the bacterial gene LAC-Z encoding β-galactosidase was used, and after three days from the injury and the application of the virus, β-Gal staining was performed on cyo-fixed carotid arteries. The staining demonstrated that the application of the virus from the lumen and the external by means of the pluronic gel resulted in the infection of the arterial wall from the intima throughout the adventitia.

Successively, using the same protocol, it was determined whether the virus encoding the $\beta ARK_{CT}$ was able to replicate in the carotid. After five days from the injury and the application of the virus, RT-PCR was performed on DNAse treated RNA extracted from rat common carotids. This analysis allowed testing of the efficacy of the virus to replicate in vivo.

Figure 4:
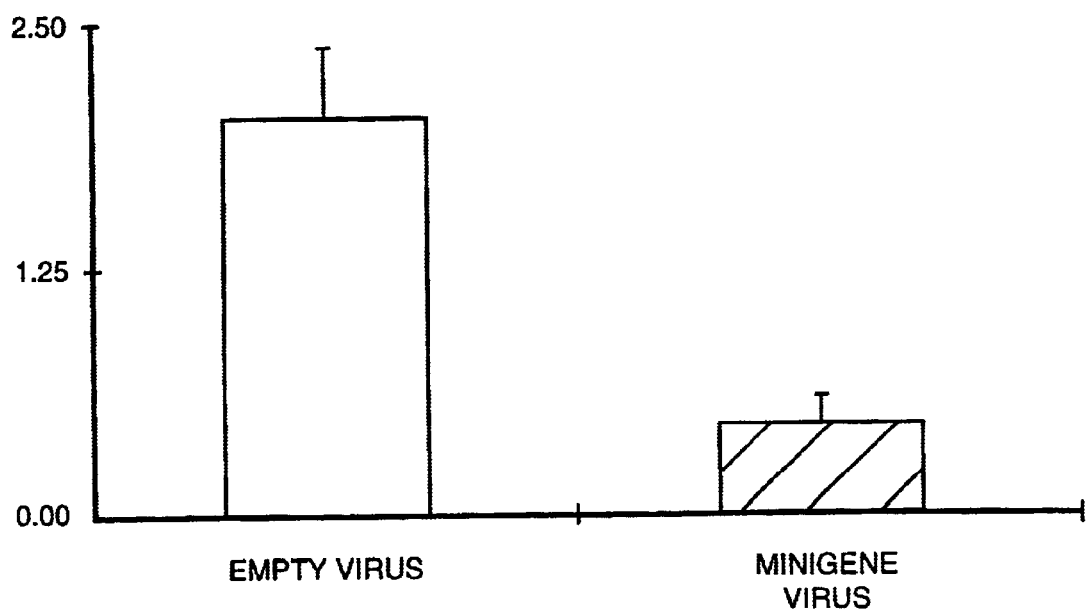
FIG. 4. Intima-to-media thickness ratio in rat carotid 28 days after balloon injury.

In a further set of experiments, injured common carotid was treated with $\beta ARK_{CT}$, or empty virus. After 28 days, the carotids were harvested and fixed and analyzed for morphometric measurements. A intimal proliferation index was obtained by the intima-to-media thickness ratio. In animals treated with empty virus, the intima proliferation was 2.036±0.312, while in the $\beta ARK_{CT}$ treated carotid, this ratio was 0.426±0.137, significantly reduced as compared to the empty virus treatment ($p<0.01$) (see FIG. 4).

All documents cited above are hereby incorporated in their entirety by reference.

One skilled in the art will appreciate from a reading of this disclosure that various changes in form and detail can be made without departing from the true scope of the invention.

What is claimed is:

1. A method of inhibiting proliferation of smooth muscle cells comprising introducing into said cells an inhibitor of Gβγ-mediated proliferative signaling in an amount and under conditions such that said inhibition of proliferation is effected.

2. The method of claim 1 wherein said smooth muscle cells are vascular smooth muscle cells.

3. The method according to claim 2 wherein said vascular cells are present in a vein graft.

4. The method according to claim 2 wherein said vascular cells are present at a carotid artery injury site.

5. The method according to claim 2 wherein said vascular cells are present at a vein graft site.

6. The method of claim 1 wherein said smooth muscle cells are airway smooth muscle cells.

7. The method of claim 1 wherein said smooth muscle cells are mammalian cells.

8. A method of screening a test compound for its ability to inhibit smooth muscle cell proliferation comprising:

contacting said test compound with βARK and Gβγ, and determining whether said test compound inhibits binding of βARK to Gβγ, wherein inhibition by said test compound of said binding is indicative of a compound that can effect said inhibition of smooth muscle cell proliferation.

9. The method according to claim 8 wherein said determination is effected by determining whether said test compound inhibits Gβγ activation of βARK.

10. A method of inhibiting pathologic proliferation of intimal vascular smooth muscle cells comprising introducing into said cells an inhibitor of Gβγ-mediated proliferative signaling in an amount and under conditions such that said inhibition of proliferation is effected.

11. A method of inhibiting proliferation of mammalian smooth muscle cells comprising introducing into said cells an inhibitor of Gβγ-mediated proliferative signaling in an amount and under conditions such that said inhibition of proliferation is effected, wherein said inhibitor binds Gαy and thereby inhibits said Gβγ-mediated proliferative signaling.

12. The method according to claim 11 wherein said inhibitor is a polypeptide.

13. The method according to claim 12 wherein a nucleic acid sequence encoding said polypeptide is introduced into said cells under conditions such that said nucleic acid is expressed and said polypeptide is thereby produced.

14. The method according to claim 11 wherein said smooth muscle cells are vascular smooth muscle cells.

15. The method according to claim 14 wherein said vascular smooth muscle cells are present in a vein graft.

16. The method according to claim 14 wherein said vascular smooth muscle cells are present at a carotid artery injury site.

17. The method according to claim 14 wherein said vascular smooth muscle cells are present at a site of insertion of a vein graft.

18. The method according to claim 11 wherein said smooth muscle cells are airway smooth muscle cells.

19. A method of inhibiting pathologic proliferation of mammalian intimal vascular smooth muscle cells comprising introducing into said cells an inhibitor of Gβγ-mediated proliferative signaling in an amount and under conditions such that said inhibition of proliferation is effected, wherein said inhibitor binds Gβγ and thereby inhibits said Gβγ-mediated proliferative signaling.

20. The method according to claim 19 wherein said inhibitor is a polypeptide.

21. The method according to claim 20 wherein said polypeptide is the Gβγ binding domain of βARK.

22. The method according to claim 20 wherein a nucleic acid sequence encoding said polypeptide is introduced into said cells under conditions such that said nucleic acid is expressed and said polypeptide is thereby produced.

23. The method according to claim 20 wherein said polypeptide has the amino acid sequence set forth in SEQ ID NO:2 or portion thereof that includes at least amino acids 150–177 of said SEQ ID NO:2 sequence.

24. The method according to claim 1 wherein said inhibitor is a polypeptide.

25. The method according to claim 24 wherein a nucleic acid sequence encoding said polypeptide is introduced into said cells under conditions such that said nucleic acid is expressed and said polypeptide is thereby produced.

26. The method according to claim 24 wherein said polypeptide has the amino acid sequence set forth in SEQ ID NO:2 or portion thereof that includes at least amino acids 150–177 of said SEQ ID NO:2 sequence.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 591 base pairs
      (B) TYPE: nucleic acid
      (C) STRANDEDNESS: single
      (D) TOPOLOGY: linear (ii) MOLECULE TYPE: DNA (genomic)

(v) FRAGMENT TYPE: linear (xi) SEQUENCE DESCRIPTION: SEQ ID NO: 1:

```
ATGGGAATCA AGCTACTGGA CAGTGACCAG GAGCTCTACC GCAACTTCCC CCTGACCATC      60

TCGGAGCGGT GGCAGCAGGA GGTAGCAGAG ACTGTCTTTG ACACCATCAA TGCTGAGACG     120

GACCGGCTGG AGGCCCGCAA GAAAACCAAA AACAAGCAGT TGGGCCACGA GGAAGACTAC     180

GCCCTGGGCA AGGACTGCAT CATGCATGGC TACATGTCCA AGATGGGCAA CCCCTTCCTG     240

ACCCAGTGGC AGCGGCGGTA CTTCTACCTG TTCCCTAACG GGCTCGAGTG GCGGGGCGAG     300

GGCGAGGCCC CGCAGAGCCT GCTGACCATG GAGGAGATCC AGTCGGTGGA GGAGACGCAG     360

ATCAAGGAGC GAAAGTGCCT CCTCCTCAAG ATCCGAGGTG GCAAGCAGTT TGTCCTGCAG     420

TGCGATAGTG ACCCAGAGCT GGTGCAGTGG AAGAAGGAGC TTCGAGACGC CTACCGCGAG     480

GCCCAGCAGC TAGTGCAGCG GGTGCCCAAG ATGAAGAACA AGCCGCGCTC GCCCGTCGTG     540
```

GAGCTGAGCA AGGTGCCACT GATCCAGCGC GGCAGTGCCA ACGGCCTCTG A          591

(2) INFORMATION FOR SEQ ID NO: 2:

(i) SEQUENCE CHARACTERISTICS:
        (A) LENGTH: 196 amino acids
        (B) TYPE: amino acid
        (C) STRANDEDNESS: <Unknown>
        (D) TOPOLOGY: linear (ii) MOLECULE TYPE: protein (v) FRAGMENT TYPE: linear (xi) SEQUENCE DESCRIPTION: SEQ ID NO: 2:

```
Met Gly Ile Lys Leu Leu Asp Ser Asp Gln Glu Leu Tyr Arg Asn Phe
1               5                   10                  15

Pro Leu Thr Ile Ser Glu Arg Trp Gln Gln Glu Val Ala Glu Thr Val
            20                  25                  30

Phe Asp Thr Ile Asn Ala Glu Thr Asp Arg Leu Glu Ala Arg Lys Lys
        35                  40                  45

Thr Lys Asn Lys Gln Leu Gly His Glu Glu Asp Tyr Ala Leu Gly Lys
    50                  55                  60

Asp Cys Ile Met His Gly Tyr Met Ser Lys Met Gly Asn Pro Phe Leu
65                  70                  75                  80

Thr Gln Trp Gln Arg Arg Tyr Phe Tyr Leu Phe Pro Asn Arg Leu Glu
                85                  90                  95

Trp Arg Gly Glu Gly Glu Ala Pro Gln Ser Leu Leu Thr Met Glu Glu
                100                 105                 110

Ile Gln Ser Val Glu Glu Thr Gln Ile Lys Glu Arg Lys Cys Leu Leu
            115                 120                 125

Leu Lys Ile Arg Gly Gly Lys Gln Phe Val Leu Gln Cys Asp Ser Asp
130                 135                 140

Pro Glu Leu Val Gln Trp Lys Lys Glu Leu Arg Asp Ala Tyr Arg Glu
145                 150                 155                 160

Ala Gln Gln Leu Val Gln Arg Val Pro Lys Met Lys Asn Lys Pro Arg
                165                 170                 175

Ser Pro Val Val Glu Leu Ser Lys Val Pro Leu Ile Gln Arg Gly Ser
            180                 185                 190

Ala Asn Gly Leu
            195
```

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO: 3:

GAATTCGCCG CCACCATGGG          20

(2) INFORMATION FOR SEQ ID NO: 4:

(i) SEQUENCE CHARACTERISTICS:
        (A) LENGTH: 22 base pairs
        (B) TYPE: nucleic acid

```
        (C) STRANDEDNESS: single
        (D) TOPOLOGY: linear (ii) MOLECULE TYPE: DNA (genomic)

(v) FRAGMENT TYPE: linear (xi) SEQUENCE DESCRIPTION: SEQ ID NO: 4:

GGAACAAAGG AACCTTTAAT AG                                               22
```